(12) United States Patent
Lee et al.

(10) Patent No.: US 8,864,948 B2
(45) Date of Patent: *Oct. 21, 2014

(54) DIVIDING WALL COLUMN FOR PRODUCING HIGH-PURITY NEOPENTYL GLYCOL AND MANUFACTURING METHOD USING SAME

(71) Applicant: LG Chem, Ltd., Seoul (KR)

(72) Inventors: Sung Kyu Lee, Daejeon (KR); Joon Ho Shin, Daejeon (KR); Jong Ku Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/929,578

(22) Filed: Jun. 27, 2013

(65) Prior Publication Data

US 2013/0292243 A1 Nov. 7, 2013

Related U.S. Application Data

(63) Continuation of application No. PCT/KR2011/010131, filed on Dec. 27, 2011.

(30) Foreign Application Priority Data

Dec. 29, 2010 (KR) .......................... 10-2010-0138239

(51) Int. Cl.
*B01D 3/14* (2006.01)
*C07C 29/80* (2006.01)
*C07C 31/20* (2006.01)
*C07B 63/00* (2006.01)

(52) U.S. Cl.
CPC ................ *B01D 3/141* (2013.01); *C07C 29/80* (2013.01); *C07B 63/00* (2013.01)
USPC ........... 202/158; 202/161; 202/262; 568/868; 568/918

(58) Field of Classification Search
USPC ........... 202/158, 161, 262; 568/868, 913, 918
See application file for complete search history.

(56) References Cited

U.S. PATENT DOCUMENTS

| | | | |
|---|---|---|---|
| 2,471,134 A * | 5/1949 | Wright | .......................... 196/111 |
| 4,021,496 A | 5/1977 | Wright | |
| 4,855,515 A | 8/1989 | Morris et al. | |
| 4,935,555 A | 6/1990 | Elias et al. | |
| 6,048,441 A * | 4/2000 | Auer et al. | ...................... 203/72 |
| 6,649,028 B2 * | 11/2003 | Sakamoto et al. | .............. 203/98 |
| 2004/0040829 A1 | 3/2004 | Gall et al. | |

FOREIGN PATENT DOCUMENTS

| | | |
|---|---|---|
| CN | 1427832 A | 7/2003 |
| CN | 1484627 A | 3/2004 |
| CN | 1678600 A | 10/2005 |
| JP | 2000-505103 A | 4/2000 |
| WO | WO 98/17614 | 4/1998 |

* cited by examiner

*Primary Examiner* — Nina Bhat
*Assistant Examiner* — Jonathan Miller
(74) *Attorney, Agent, or Firm* — McKenna Long & Aldridge LLP (57) ABSTRACT

Disclosed is a dividing wall column for preparing high-purity neopentyl glycol, and a method of distilling neopentyl glycol. Using only one column, the dividing wall column has the same effect as when using two columns. Thus, energy and equipment costs may be reduced in the production of the high-purity neopentyl glycol as compared to a conventional process apparatus.

10 Claims, 4 Drawing Sheets

Fig. 1

PRIOR ART

Fig. 2

PRIOR ART

Fig. 3

PRIOR ART

Fig. 4

PRIOR ART

DIVIDING WALL COLUMN FOR PRODUCING HIGH-PURITY NEOPENTYL GLYCOL AND MANUFACTURING METHOD USING SAME

This application is a Continuation Bypass Application of International Application No. PCT/KR2011/010131, filed Dec. 27, 2011, and claims the benefit of Korean Application No. 10-2010-0138239 filed on Dec. 29, 2010, all of which are hereby incorporated by reference in their entirety for all purposes as if fully set forth herein.

TECHNICAL FIELD

The present invention relates to a dividing wall column for preparing high-purity neopentyl glycol and a preparation method using the same.

BACKGROUND ART

Since various raw materials such as crude oil are typically mixtures of many compounds in many cases, such various raw materials are often used after being separated into compounds, instead of directly industrially used. A representative process from among chemical processes for separating a mixture is a distillation process. In general, since a distillation process separates a raw material into a high boiling component and a low boiling component, when the number of components of a mixture to be separated is n, the number of distillation columns is n−1 which is obtained by subtracting 1 from the number (n). That is, a process for separating a high-purity product from a crude raw material in the conventional distillation industry mostly uses a structure in which 2 distillation columns are continuously arranged.

Figure 1:
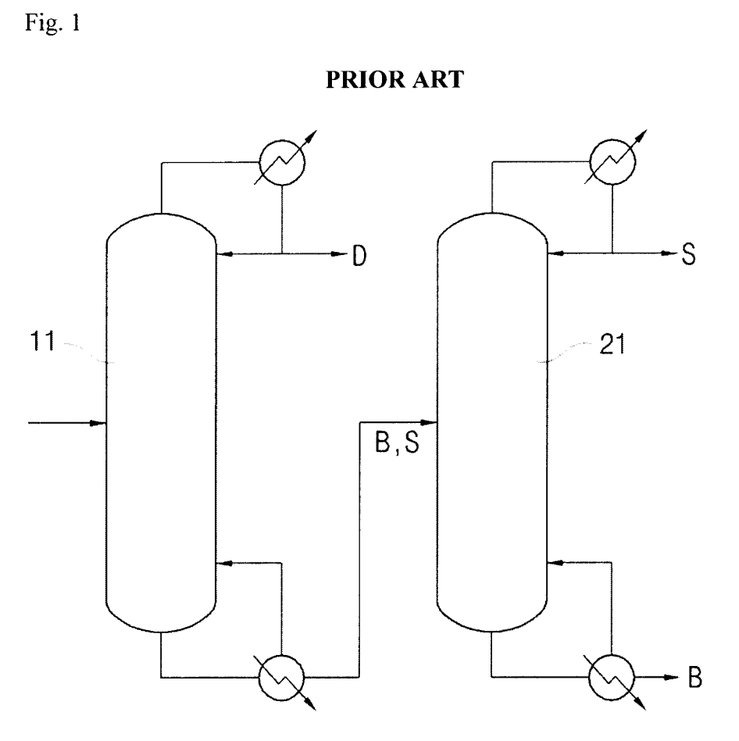
FIG. 1 is a schematic view illustrating a distillation process of a 2-column method for preparing high-purity neopentyl glycol.

As shown in FIG. 1, a conventional distillation process uses a 2-column method of separating a low boiling component D in a first column 11, and separating a medium boiling component S and a high boiling component B in a second column 21.

Figure 2:
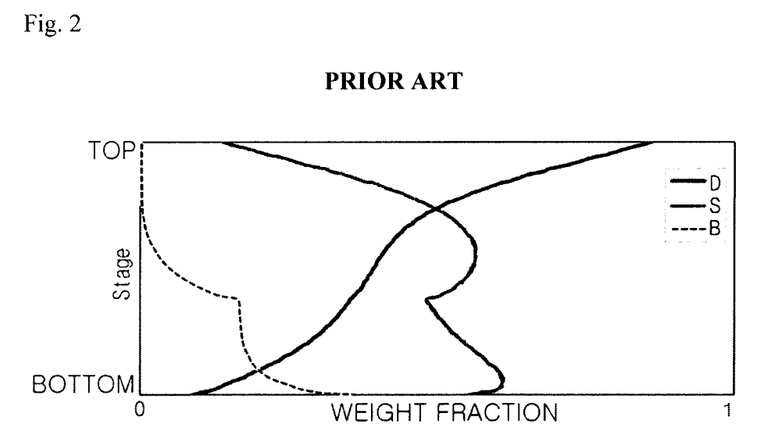
FIG. 2 shows a graph illustrating a composition profile in a first column in the distillation process of the 2-column method.
Figure 3:
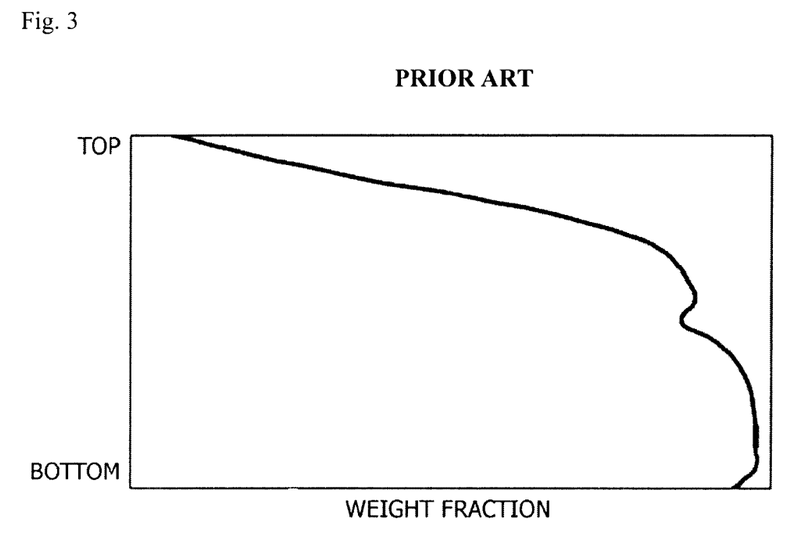
FIG. 3 shows a graph illustrating a composition profile of neopentyl glycol in the first column in the distillation process of the 2-column method.

A composition profile in a first column in a conventional 2 column distillation method which is a typical process of distilling alcohols is shown in FIG. 2. As shown in FIG. 2, the medium boiling component B is generally re-mixed in a lower part of the first column. In particular, when neopentyl glycol is separated as a medium boiling component, a composition profile in the first column is shown in FIG. 3. As shown in FIG. 3, even when neopentyl glycol is used, the medium boiling component is re-mixed in a lower part of the first column.

Although the conventional distillation process may easily control a composition of a product, the conventional distillation process has problems in that a medium boiling component is re-mixed and diluted in a first distillation column. This remixing effect leads to additionally unnecessary energy consumptions because of a thermal inefficiency.

Figure 4:
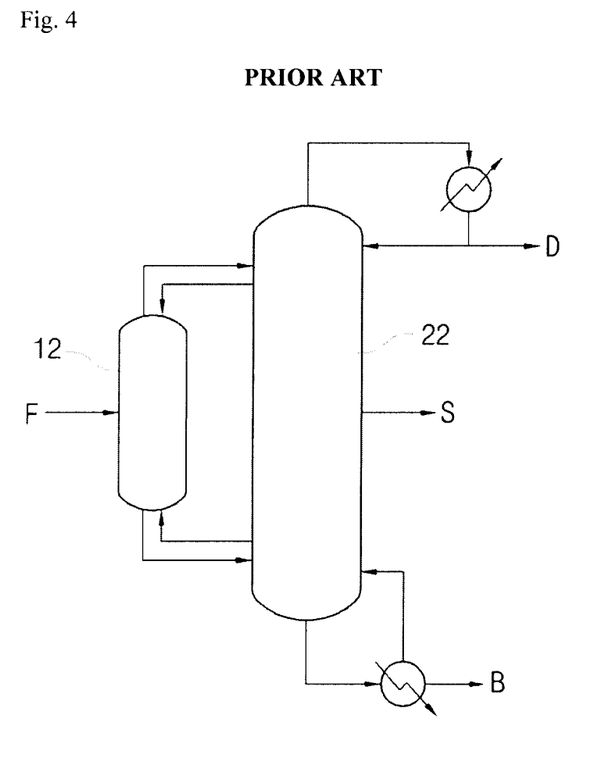
FIG. 4 is a schematic view illustrating an internal structure of a Petlyuk distillation column.

In order to solve these problems, many studies have been done on a new distillation structure. A representative attempt to improve separation efficiency through a thermally coupled structure is a Petlyuk distillation column structure as shown in FIG. 4. A Petlyuk distillation column includes a pre-fractionator 12 and a main column 22 which are thermally coupled to each other such that a low boiling component and a high boiling component are first separated in the pre-fractionator 12, then a top portion and a bottom portion of the pre-fractionator 12 are respectively loaded into inflow plates of the main column 22, and a low boiling component D, a medium boiling component S, and a high boiling component B are separated from one another in the main column 22. In the Petlyuk distillation column structure, since a distillation curve in the Petlyuk distillation column is similar to an equilibrium distillation curve, energy efficiency is high. However, it is not easy to design a process and operate the Petlyuk distillation column, and it is particularly difficult to balance a pressure in the Petlyuk distillation column.

DISCLOSURE

Technical Problem

The present invention is directed to providing a dividing wall column for preparing high-purity neopentyl glycol and a preparation method using the same.

Technical Solution

One aspect of the present invention provides a dividing wall column including a main column including: a condenser; a reboiler; and a dividing wall, wherein the main column is divided into a top zone, an upper inflow zone, an upper outflow zone, a lower inflow zone, a lower outflow zone, and a bottom zone, and includes at least one inflow stream and at least three outflow streams, wherein each of the at least one inflow stream is a stream that a feed containing crude neopentyl glycol flows into an inflow middle plate where the upper inflow zone and the lower inflow zone of the main column contact each other, and one or more of the at least three outflow streams is a stream of neopentyl glycol, and a method of preparing high-purity neopentyl glycol using the dividing wall column.

Advantageous Effects

A dividing wall column according to the present invention may provide an effect of having two distillation columns using one distillation column, and may reduce energy consumption and equipment costs when compared to a conventional process apparatus for preparing high-purity neopentyl glycol.

BEST MODE OF THE INVENTION

A dividing wall column according to the present invention includes a main column including a condenser, a reboiler, and a dividing wall, wherein the main column is divided into a top zone, an upper inflow zone, an upper outflow zone, a lower inflow zone, a lower outflow zone, and a bottom zone, and includes at least one inflow stream and at least three outflow streams, wherein each of the at least one inflow stream is a stream that a feed F containing crude neopentyl glycol flows into an inflow middle plate NR1 where the upper inflow zone and the lower inflow zone of the main column contact each other, and one or more of the at least three outflow streams is a stream of neopentyl glycol.

The dividing wall column is equivalent to a Petlyuk distillation column in a thermodynamic aspect, but is different from the Petlyuk distillation column in a structural aspect because a dividing wall is provided in a column to integrate a pre-fractionator in a main column. Since the dividing wall column naturally solves a difficulty in balancing a pressure between the pre-fractionator and the main column and a difficulty in performing an operation, an operation may be facilitated. Also, since two distillation columns are integrated into one, investment costs may be significantly reduced.

Also, a dividing wall column according to the present invention includes a main column including a condenser, a reboiler, and a dividing wall, wherein the main column is divided into a top zone, an upper inflow zone, an upper outflow zone, a lower inflow zone, a lower outflow zone, and a bottom zone, wherein a feed F containing crude neopentyl glycol flows into an inflow middle plate NR1 where the upper inflow zone and the lower inflow zone of the main column contact each other, a lower boiling component D flows out to the top zone, a high boiling component B flows out to the bottom zone, and a medium boiling component S flows out to an outflow middle plate NR2 where the upper outflow zone and the lower outflow zone contact each other.

The middle boiling component may be substantially neopentyl glycol.

The feed F may have a neopentyl glycol content greater than or equal to 80 wt %.

Figure 5:
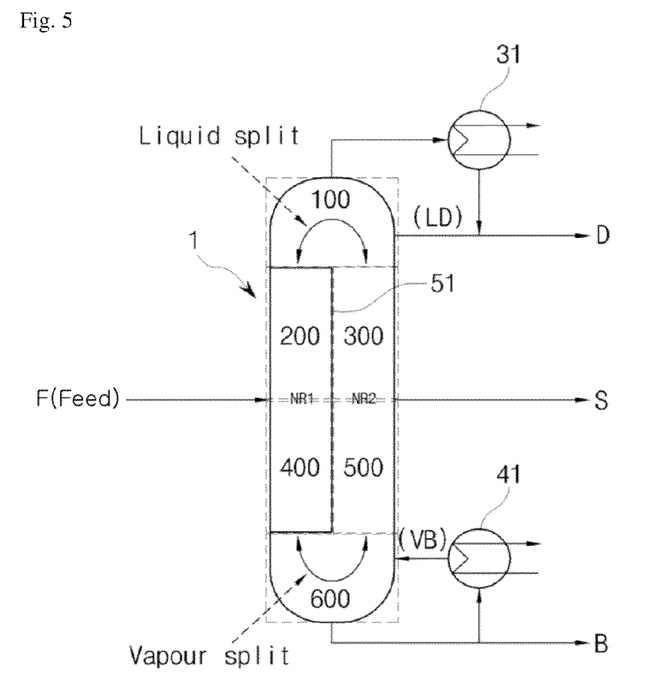
FIG. 5 is a schematic view illustrating a structure of a dividing wall column according to an embodiment of the present invention.

FIG. 5 is a schematic view illustrating a dividing wall column according to an embodiment of the present invention. Referring to FIG. 5, the dividing wall column includes a main column 1, and a condenser 31 and a reboiler 41 respectively connected to an upper end and a lower end of the main column 1.

The condenser 31 is a device for depriving evaporation heat of a mixture in a gaseous state and condensing the mixture. A condenser used in a conventional chemical engineering system may be used without limitation. Also, the reboiler 41 is a device for providing evaporation heat to a mixture in a liquid state and evaporating the mixture. A reboiler used in a conventional chemical engineering system may be used without limitation.

The main column 1 may be roughly divided into 6 zones. A top zone 100 refers to an upper area of the main column 1 with no dividing wall. An upper inflow zone 200 is one of areas divided by a dividing wall and a sub-area located over a stream of an inflow component (feed). An upper outflow zone 300 is one of the areas divided by the dividing wall and is a sub-area located over a stream of an outflow component. A lower inflow zone 400 is one of the areas divided by the dividing wall and is a sub-area located under the stream of the inflow component. A lower outflow zone 500 is one of the areas divided by the dividing wall, and is a sub-area located under the stream of the outflow component. Also, a bottom zone 600 refers to a lower area of the main column 1 with no dividing wall.

Also, the main column 1 has at least one inflow stream and at least three outflow streams. The at least one inflow stream includes a stream in which a feed F which is crude neopentyl glycol flows into an inflow middle plate NR1 where the upper inflow zone 200 and the lower inflow zone 400 of the main column 1 contact each other. The at least three outflow streams may include streams in which a low boiling component D flows out to the top zone 100, a high boiling component B flows out to the bottom zone 600, and a medium boiling component S flows out to an outflow middle plate NR2 where the upper outflow zone 300 and the lower outflow zone 500 contact each other. In this case, the medium boiling component S flowing out to the outflow middle plate NR2 may be substantially neopentyl glycol.

The term 'crude neopentyl glycol feed' used herein which is a mixture having neopentyl glycol as a main component refers to a target material to be distilled in a distillation process, and the term 'main component' used herein refers to one component which is included in the largest amount among respective components of the mixture. In order to obtain high-purity neopentyl glycol, it is preferable that a crude neopentyl glycol feed has a higher neopentyl glycol content. In order to obtain high-purity neopentyl glycol greater than or equal to 99 wt %, it is preferable that a crude neopentyl glycol feed has a neopentyl glycol content greater than or equal to 55 wt %.

Also, the expression 'substantially neopentyl glycol' means that a mixture may be regarded as substantially neopentyl glycol. In detail, the expression 'substantially neopentyl glycol' means that a mixture has neopentyl glycol as a main component, has a higher neopentyl glycol content than a feed, and has a neopentyl glycol component exceeding at least 90 wt % with respect to a whole mixture.

A dividing wall-type distillation process has an advantage of lower energy consumption than a conventional process using 2 continuous distillation columns due to a structural difference. In the dividing wall column, since spaces divided by the dividing wall act as a pre-fractionator, a composition of a liquid is almost similar to an equilibrium distillation curve due to separation of a high boiling component and a low boiling component, and thermodynamic efficiency for separation is improved due to suppression of re-mixing.

The upper inflow zone and the lower inflow zone substantially act as a pre-fractionator of a conventional process. That is, the upper inflow zone and the lower inflow zone may be collectively referred to as a pre-separation area. A feed flowing into the pre-separation area is separated into a low boiling component and a high boiling component. Some of the low boiling component and the high boiling component separated in the pre-separation area flows into the top zone, and some flows back into the upper outflow zone and the lower outflow zone to be re-distilled.

The upper outflow zone and the lower outflow zone act as a main column of a conventional process. That is, the upper outflow zone and the lower outflow zone may be collectively referred to as a main separation area. A low boiling component and a medium boiling component are mainly separated in an upper portion of the dividing wall of the main separation area, and a medium boiling component and a high boiling component are mainly separated in a lower portion of the dividing wall of the main separation area.

Figure 6:
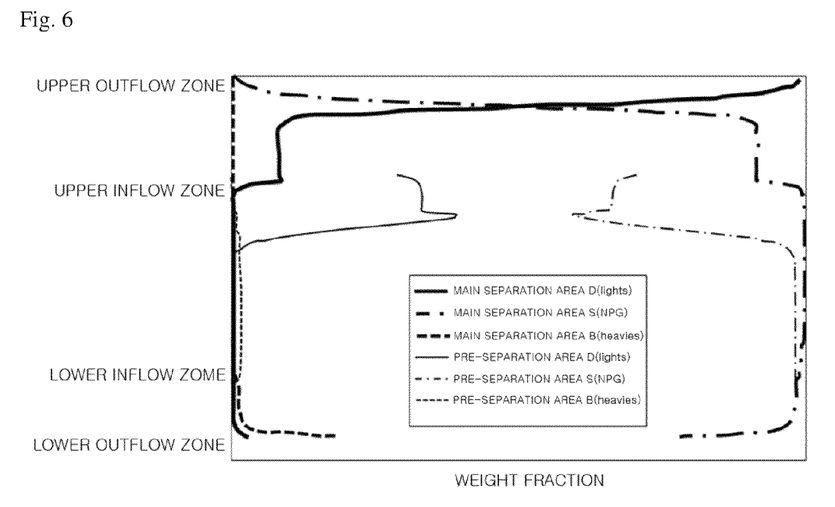
FIG. 6 shows a graph illustrating a composition profile in a column of the dividing wall column of FIG. 5.

In detail, a composition profile in the dividing wall column of FIG. 5 is shown in FIG. 6.

The low boiling component D passes through the top zone of the main column and the condenser, and some of the low boiling component D is produced into a low boiling product and the remaining returns as a liquid flux LD to the top zone of the main column. Also, the high boiling component B passes through the bottom zone of the main column and the reboiler, and some of the high boiling component B is produced into a high boiling product and the remaining returns as a vapor flux VB to the bottom zone of the main column.

A design of a thermally coupled distillation column system having a dividing wall is based on a design of a conventional thermally coupled distillation column and a design of a distillation column having a minimum number of plates. Since separation efficiency of a distillation column is maximized when a liquid compositional distribution of distillation plates in the distillation column is similar to an equilibrium distillation curve, a minimum-plate distillation system is first designed under the assumption that a distillation column is operated by handling a pre-reflux. That is, the upper inflow zone and the lower inflow zone are designed under the assumption that compositions of a feed and a liquid at a feed inflow plate are the same. In the upper outflow zone and the lower outflow zone, a composition of a liquid in the dividing wall column from the middle to the top is calculated by a cascade method of designing an equilibrium composition starting from a concentration of a medium boiling product. In the lower outflow zone acting as a main column, a composition of a liquid in the dividing wall column is calculated from the middle to the bottom using a cascade method of calculating an equilibrium composition starting from a concentration of the medium boiling product.

The number of plates of each of the upper inflow zone and the lower inflow zone which act as a pre-fractionator and the upper outflow zone and the lower outflow zone which act as a main column may be obtained by calculating the number of plates having a composition of a product and the number of feed inflow plates from a distribution of the obtained composition of the liquid. Since the number of plates is an ideal theoretical plate number, the actual number of plates in the dividing wall column may vary according to a common design standard.

In the dividing wall column according to the present embodiment, the number of plates provided in each of the top zone, the upper inflow zone, the upper outflow zone, the lower inflow zone, the lower outflow zone, and the bottom zone may range from 90 to 140% of a theoretical plate number which is calculated from a distillation curve. When the number of plates is less than 90% of the calculated theoretical plate number, a low boiling component and a high boiling component may not be well separated in the pre-separation area, and when the number of plates exceeds 140%, energy consumption reduction is no longer increased in an area having a minimum reflux ratio, resulting in an increase in investment costs.

Also, a length of the dividing wall provided in the main column is determined according to a plate number calculated according to distillation curves of the upper inflow zone and the lower inflow zone, or the upper outflow zone and the lower outflow zone. While there are various methods of obtaining a theoretical plate number and a reflux amount by determining a spacing of the dividing wall using an equilibrium distillation curve method on a liquid composition with the pre-separation area and the main separation area when an optimal spacing of the dividing wall is designed in the dividing wall column, a theoretical plate number is obtained using a Fenske-Underwood method in the present invention. The Fenske-Underwood method is well known to one of ordinary skill in the art.

A length of the dividing wall may range from 40 to 85% of a total theoretical plate number of the top zone, the upper inflow zone, the lower outflow zone, and the bottom zone calculated from a distillation curve. When the length of the dividing wall is less than 40%, some of a low boiling component in the pre-separation area may flow down from the pre-separation area and may be introduced into a product in the main column. When the length of the dividing wall exceeds 85%, it is difficult to maintain a smooth equilibrium flow of liquid/vapor states of low boiling/medium boiling components and liquid/vapor states of medium boiling/high boiling components in the dividing wall column, thereby making it difficult to manufacture a distillation column.

A condition for operating the dividing wall column for preparing high-purity neopentyl glycol is as follows.

For example, a temperature of the top zone preferably ranges from 110 to 120° C. at a pressure of the top zone of −0.85 to −0.75 kg/sqcmG. When the temperature of the top zone is less than 110° C., a low boiling component may flow down from the pre-separation area, thereby badly affecting product purity. When the temperature of the top zone exceeds 120° C., a high boiling component (Heavies) may flow up from the pre-separation area, thereby badly affecting product purity.

A temperature of the bottom zone preferably ranges from 172 to 182° C. at a pressure of the top zone of −0.85 to −0.75 kg/sqcmG. When the temperature of the bottom zone is less than 172° C., a medium boiling component may flow down, thereby reducing productivity. When the temperature of the bottom zone exceeds 182° C., the high boiling component (Heavies) may laterally flow along with the medium boiling component.

Also, a temperature of the outflow middle plate NR2 which is located at a position where the upper outflow zone and the lower outflow zone contact each other and to which the medium boiling component S flows out preferably ranges from 170 to 178° C. at a pressure of the top zone of −0.85 to −0.75 kg/sqcmG. When the temperature of the outflow middle plate NR2 is less than 170° C., it is not easy to remove a low boiling component. When the temperature of the outflow middle plate NR2 exceeds 178° C., it is not easy to remove a high boiling component, thereby greatly affecting product purity.

When the dividing wall column is depressurized or pressurized, the temperature ranges may be changed. In general, as a pressure increases, an upper temperature limit and a lower temperature limit tend to increase. A relationship between a temperature and a pressure may be represented by Equations 1 through 3.

A temperature of the top zone may range from a lower temperature limit $T_{1a}$ to an upper temperature limit $T_{2a}$ according to Equation 1.

Lower temperature limit: $T_{1a}=487.01P^2+894.48P+515$

Upper temperature limit: $T_{2a}=487.01P^2+894.48P+525$ (1), wherein $T_{1a}$ and $T_{2a}$ are temperatures (° C.), and P is a pressure of the top zone (kg/sqcmG), provided that $-0.95 \leq P \leq -0.65$.

A temperature of the bottom zone may range from a lower temperature limit $T_{1b}$ to an upper temperature limit $T_{2b}$ according to Equation 2.

Lower temperature limit: $T_{1b}=519.48P^2+920.78P+577$

Upper temperature limit: $T_{2b}=519.48P^2+920.78P+587$ (2), wherein $T_{1b}$ and $T_{2b}$ are temperatures (° C.), and P is a pressure of the top zone (kg/sqcmG), provided that $-0.95 \leq P \leq -0.65$.

Also, a temperature of the outflow middle plate NR2 which is located at a position where the upper outflow zone and the lower outflow zone contact each other and to which the medium boiling component S flows out may range from a lower temperature limit $T_{1c}$ to an upper temperature limit $T_{2c}$ according to Equation 3.

Lower temperature limit: $T_{1c}=32.468P^2+126.3P+251$

Upper temperature limit: $T_{2c}=32.468P^2+126.3P+259$ (3), wherein $T_{1c}$ and $T_{2c}$ are temperatures (° C.), and P is a pressure of the top zone (kg/sqcmG), provided that $-0.95 \leq P \leq -0.65$.

A thermally coupled distillation column system having a dividing wall according to the present invention has an objective of improving energy efficiency of distilling a 3-component mixture, and has an effect of having two distillation columns by providing the dividing wall in a main column to form spaces which function as a pre-fractionator and a main column having a liquid composition distribution similar to that of a high-efficiency equilibrium distillation system.

Also, the present invention provides a method of preparing neopentyl glycol using the dividing wall column. The method may prepare high-purity neopentyl glycol by providing a crude neopentyl glycol feed to the dividing wall column and separately distilling neopentyl glycol.

The dividing wall column includes the main column including the condenser, the reboiler, and the dividing wall, wherein the main column is divided into the top zone, the upper inflow zone, the upper outflow zone, the lower inflow zone, the lower outflow zone, and the bottom zone, and includes at least one inflow stream and at least three outflow streams, wherein each of the at least one inflow stream is a stream that the feed F containing crude neopentyl glycol flows into the inflow middle plate NR1 where the upper inflow zone and the lower inflow zone of the main column contact each other, and the at least three outflow streams include streams in which the low boiling component D flows out to the top zone, the high boiling component B flows out to the bottom zone, and the medium boiling component S flows out to the outflow middle plate NR2 where the upper outflow zone and the lower outflow zone contact each other and the medium boiling component S flowing out to the outflow middle plate NR2 is substantially neopentyl glycol.

[Modes of the Invention]

Hereinafter, exemplary embodiments of the present invention will be described in detail. However, the present invention is not limited to the exemplary embodiments disclosed below, but can be implemented in various forms.

Embodiment and Comparative Example

A dividing wall column was designed, manufactured, and operated in order to verify a performance of a system according to the present invention. It was found from the operation of the dividing wall column that a desired product composition was obtained. For a comparative example, conventional 2 distillation columns having no dividing wall were used, and for an embodiment, 1 distillation column having a dividing wall was used.

Figure 7:
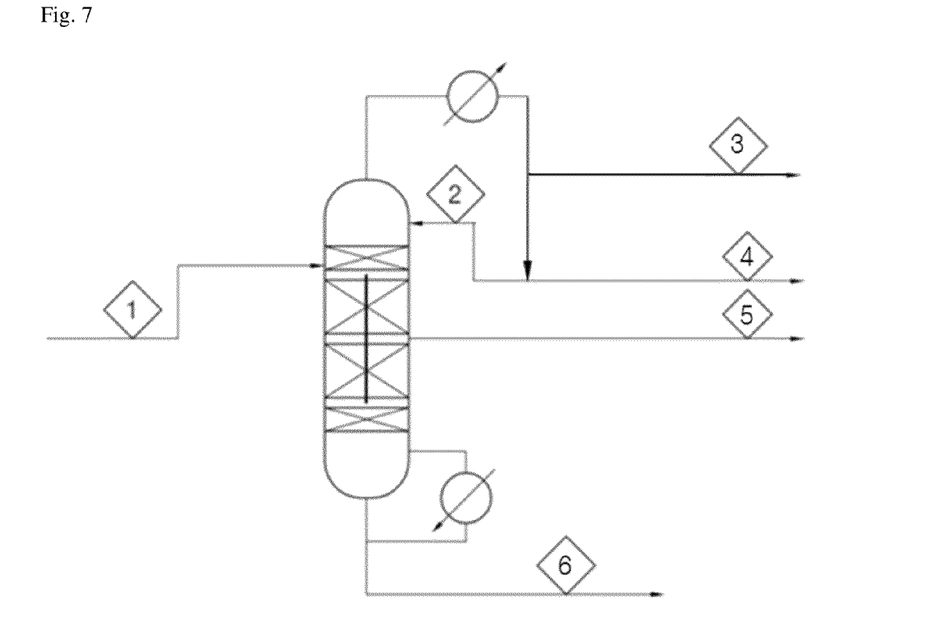
FIG. 7 is a schematic view illustrating a process of distilling neopentyl glycol using the dividing wall column of FIG. 5.
Figure 8:
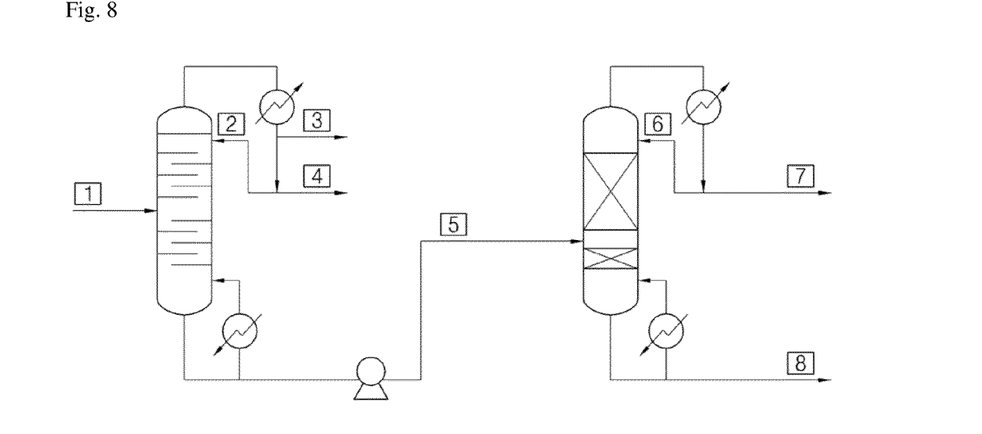
FIG. 8 is a schematic view illustrating a process of distilling neopentyl glycol using a distillation column of a 2-column method.

FIGS. 6 and 7 are schematic views illustrating the embodiment of the present invention and the comparative example, respectively. FIG. 6 illustrates a dividing wall column according to the embodiment of the present invention. FIG. 7 illustrates a conventional distillation column including 2 columns according to the comparative example. In FIGS. 6 and 7, reference numerals 1 to 8 denote individual streams in the embodiment and the comparative example.

The embodiment and the comparative example have theoretical plate numbers as shown in Table 1, and experimental results are shown in Tables 2 and 3. Table 2 shows a condition and a composition of each stream according to the embodiment. Table 3 shows a condition and a composition of each stream according to the comparative example.

TABLE 1

|  | Item | Theoretical plate number |
|---|---|---|
| Embodiment | Top zone 100 | 20 |
|  | Upper inflow zone 200 | 8 |
|  | Upper outflow zone 300 | 20 |
|  | Lower inflow zone 400 | 25 |
|  | Lower outflow zone 500 | 10 |
|  | Bottom zone 600 | 10 |
| Comparative example | First column | 35 |
|  | Second column | 30 |

TABLE 2

| Embodiment | | Stream number | | | | | |
|---|---|---|---|---|---|---|---|
|  |  | 1 | 2 | 3 | 4 | 5 | 6 |
| Condition | Temperature (° C.) | 147 | 50.1 | 50.1 | 50.1 | 152.5 | 182.4 |
|  | Pressure (kg/sqcmG) | 5.00 | −0.89 | −0.89 | −0.89 | −0.92 | −0.71 |
|  | flux (kg/hr) | 23302.6 | 14500 | 2427.3 | 6759.7 | 13100 | 1015.79 |
| Composition | Low boiling point (wt %) | 39.30 | 99.30 | 99.60 | 99.30 | 0.10 | 2.90 |
|  | Medium boiling point (NPG)(wt %) | 59.30 | 0.40 | 0.40 | 0.70 | 99.80 | 78.50 |
|  | High boiling point (wt %) | 1.40 | 0.00 | 0.00 | 0.00 | 0.10 | 18.60 |
|  | Sum (wt %) | 100 | 100 | 100 | 100 | 100 | 100 |

TABLE 3

| Comparative example | | Stream number | | | | | | | |
|---|---|---|---|---|---|---|---|---|---|
| | | 1 | 2 | 3 | 4 | 5 | 6 | 7 | 8 |
| Condition | Temperature (° C.) | 147.1 | 50.1 | 50.1 | 50.1 | 173.5 | 152.5 | 152.5 | 170.3 |
| | Pressure (kg/sqcmG) | 3 | −0.885 | −0.885 | −0.885 | −0.764 | −0.924 | −0.924 | −0.846 |
| | flux (kg/hr) | 23002.8 | 16713 | 2444.6 | 6559.2 | 13999 | 2000 | 12954.1 | 899 |
| Composition | Low boiling point (wt %) | 39.30 | 99.40 | 99.50 | 99.40 | 0.50 | 0.40 | 0.40 | 2.20 |
| | Medium boiling point (wt %) | 59.30 | 0.60 | 0.50 | 0.60 | 97.00 | 99.40 | 99.40 | 61.40 |
| | High boiling point (wt %) | 1.40 | 0.00 | 0.00 | 0.00 | 2.50 | 0.20 | 0.20 | 36.40 |
| | Sum (wt %) | 100 | 100 | 100 | 100 | 100 | 100 | 100 | 100 |

When Table 2 and Table 3 are compared with each other, when the dividing wall column according to the embodiment was used, high-purity neopentyl glycol of 99.8 wt % was more efficiently obtained due to removal of re-mixing and an increase in separation efficiency. An additional recycling process of rectifying neopentyl glycol is reduced due to an increase in product purity, thereby improving productivity.

Also, Table 4 shows a result obtained by measuring energy consumption according to the embodiment and the comparative example (conventional) and calculating a reduction rate.

TABLE 4

| | Comparative example | | | Embodiment | Reduced amount (MMK cal/hr) | Reduction rate (%) |
|---|---|---|---|---|---|---|
| Energy consumption (MMK cal/hr) | First column: 4.63 | Second column: 2.35 | Sum: 6.98 | 4.48 | 2.5 | 35.8 |

The comparative example using the conventional distillation column includes 2 columns and 4 heat exchangers whereas the dividing wall column according to the embodiment may include 1 column and 2 heat exchangers. Accordingly, investment costs of the dividing wall column according to the embodiment of the present invention may be about 30% lower than those of the conventional distillation column. In particular, an energy reduction rate of the dividing wall column according to the embodiment of the present invention is about 35.8% lower than that of the conventional distillation column.

DESCRIPTION OF REFERENCE NUMERALS

1: main column
11: first column
21: second column
12: pre-fractionator
22: main column
31: condenser
41: reboiler
51: dividing wall
100: top zone
200: upper inflow zone
300: upper outflow zone
400: lower inflow zone
500: lower outflow zone
600: bottom zone
NR1: inflow middle plate
NR2: outflow middle plate
F: raw material (feed)
B: high boiling component
D: low boiling component
S: medium boiling component

[Industrial Applicability]

A dividing wall column according to the present invention may be variously used in fields using neopentyl glycol.

The invention claimed is:

1. A dividing wall column comprising a main column comprising:
   a condenser that is connected to an upper end of the main column;
   a reboiler that is connected to a lower end of the main column; and
   a dividing wall that is in the main column and divides the main column into a top zone, an upper inflow zone, an upper outflow zone, a lower inflow zone, a lower outflow zone, and a bottom zone,
   wherein the main column comprises an inflow middle plate where the upper and lower inflow zones contact with each other and an outflow middle plate where the upper and lower outflow zones contact with each other,
   wherein the top zone is an upper area of the main column with no dividing wall, the upper inflow zone is one of a plurality of areas divided by the dividing wall and is located above the inflow middle plate, the upper outflow zone is one of the plurality of areas divided by the dividing wall and is located above the outflow middle plate, the lower inflow zone is one of the plurality of areas divided by the dividing wall and is located under the inflow middle plate, the lower outflow zone is one of the plurality of areas divided by the dividing wall and is located under the outflow middle plate, and the bottom zone is a lower area of the main column with no dividing wall,
   wherein the main column is installed such that an inflow stream, that is a feed comprising crude neopentyl glycol, can flows into the inflow middle plate and then, is separated into a low boiling component flowing out to the top zone, a medium boiling component flowing out to the outflow middle plate and a high boiling component flowing out to the bottom zone, wherein at least one of the low, medium and high boiling components includes neopentyl glycol.

2. The dividing wall column of claim 1, wherein the medium boiling component flowing out to the outflow middle plate is neopentyl glycol.

3. The dividing wall column of claim 1, wherein the feed has a neopentyl glycol content greater than or equal to 55 wt %.

4. The dividing wall column of claim 1, wherein a number of plates provided in each of the top zone, the upper outflow zone, the lower inflow zone, the lower outflow zone, and the bottom zone of the main column ranges from 90 to 140% of a theoretical plate number calculated from a distillation curve.

5. The dividing wall column of claim 1, wherein a length of the dividing wall is determined according to a number of plates included in the upper inflow zone and the lower inflow zone, or the upper outflow zone and the lower outflow zone.

6. The dividing wall column of claim 1, wherein a length of the dividing wall ranges from 40 to 85% of a total theoretical plate number of the top zone, the upper inflow zone, the lower outflow zone, and the bottom zone which is calculated from a distillation curve.

7. The dividing wall column of claim 1, wherein a temperature of the top zone ranges from a lower temperature limit $T_{1a}$ to an upper temperature limit $T_{2a}$ satisfying Equation 1:

$$T_{1a}=487.01P^2+894.48P+515$$

$$T_{2a}=487.01P^2+894.48P+525 \quad \text{[Equation 1]}$$

wherein $T_{1a}$ and $T_{2a}$ are temperatures (° C.), and P is a pressure in the top zone (kg/sqcmG), provided that $-0.95 \leq P \leq -0.65$.

8. The dividing wall column of claim 1, wherein a temperature of the bottom zone ranges from a lower temperature limit $T_{1b}$ to an upper temperature limit $T_{2b}$ satisfying Equation 2:

$$T_{1b}=519.48P^2+920.78P+577$$

$$T_{2b}=519.48P^2+920.78P+587 \quad \text{[Equation 2]}$$

wherein $T_{1b}$ and $T_{2b}$ are temperatures (° C.), and P is a pressure in the top zone (kg/sqcmG), provided that $-0.95 \leq P \leq -0.65$.

9. The dividing wall column of claim 1, wherein a temperature of an outflow middle plate which is provided at a position where the upper outflow zone and the lower outflow zone contact each other and to which a medium boiling component flows out ranges from a lower temperature limit $T_{1c}$ to an upper temperature limit $T_{2c}$ satisfying Equation 3:

$$T_{1c}=32.468P^2+126.3P+251$$

$$T_{2c}=32.468P^2+126.3P+259 \quad \text{[Equation 3]}$$

wherein $T_{1c}$ and $T_{2c}$ are temperatures (° C.), and P is a pressure in the top zone (kg/sqcmG), provided that $-0.95 \leq P \leq -0.65$.

10. A method for preparing neopentyl glycol using the dividing wall column of claim 1, comprising:
   feeding the feed comprising crude neopentyl glycol into the inflow middle plate where the upper inflow zone and the lower inflow zone of the main column contact each other, and
   obtaining the neopentyl glycol from the one or more of the outflow streams.

* * * * *